(12) United States Patent
Zhang et al.

(10) Patent No.: US 9,487,558 B2
(45) Date of Patent: Nov. 8, 2016

(54) SHORT BIO-ACTIVE PEPTIDES FOR PROMOTING WOUND HEALING

(71) Applicant: HELIX BIOMEDIX, INC., Bothell, WA (US)

(72) Inventors: Lijuan Zhang, Kenmore, WA (US); Robin Carmichael, Redmond, WA (US)

(73) Assignee: HELIX BIOMEDIX INC., Bothell, WA (US)

( * ) Notice: Subject to any disclaimer, the term of this patent is extended or adjusted under 35 U.S.C. 154(b) by 0 days.

(21) Appl. No.: 14/762,407

(22) PCT Filed: Jan. 21, 2014

(86) PCT No.: PCT/US2014/012378
§ 371 (c)(1),
(2) Date: Jul. 21, 2015

(87) PCT Pub. No.: WO2014/126681
PCT Pub. Date: Aug. 21, 2014

(65) Prior Publication Data
US 2015/0353605 A1    Dec. 10, 2015

Related U.S. Application Data

(60) Provisional application No. 61/764,913, filed on Feb. 14, 2013.

(51) Int. Cl.
| | | |
|---|---|---|
| *A61K 38/00* | (2006.01) | |
| *A61K 38/07* | (2006.01) | |
| *A61K 38/08* | (2006.01) | |
| *A61K 8/64* | (2006.01) | |
| *A61Q 19/00* | (2006.01) | |
| *A61Q 19/08* | (2006.01) | |
| *C07K 7/06* | (2006.01) | |
| *C07K 5/113* | (2006.01) | |
| *C07K 5/103* | (2006.01) | |
| *C07K 14/435* | (2006.01) | |

(52) U.S. Cl.
CPC . *C07K 7/06* (2013.01); *A61K 8/64* (2013.01); *A61Q 19/00* (2013.01); *A61Q 19/08* (2013.01); *C07K 5/1013* (2013.01); *C07K 5/1021* (2013.01); *C07K 14/43563* (2013.01); *A61K 38/00* (2013.01); *A61K 2800/74* (2013.01)

(58) Field of Classification Search
CPC .. A61K 2800/74; A61K 38/00; A61K 38/07; A61K 38/08; A61K 8/64; A61Q 19/00; A61Q 19/08; C07K 7/06
USPC .............. 514/18.6, 18.8, 21.8, 21.9; 530/330
See application file for complete search history.

(56) References Cited

U.S. PATENT DOCUMENTS

| | | | | |
|---|---|---|---|---|
| 7,696,174 B2* | 4/2010 | Harris | .............. | C07K 14/43563 424/78.06 |
| 9,040,662 B2* | 5/2015 | Khaled | .............. | A61K 38/1761 530/326 |
| 2008/0206160 A1* | 8/2008 | Harris | .............. | C07K 14/43563 424/45 |
| 2014/0255299 A1* | 9/2014 | Khaled | .............. | A61K 38/1761 424/1.11 |
| 2015/0359841 A1* | 12/2015 | Khaled | .............. | A61K 38/1761 424/489 |

FOREIGN PATENT DOCUMENTS

| | | |
|---|---|---|
| EP | 0257656 A2 | 3/1988 |
| WO | 2007/146269 A2 | 12/2007 |
| WO | 2008/085494 A1 | 7/2008 |

OTHER PUBLICATIONS

Water from http://www.biology-online.org/dictionary/Water, pp. 1-3. Accessed Apr. 24, 2014.*
PCT/US2014/012378—International Search Report and Written Opinion dated Mar. 27, 2014.
Falla, Timothy, et al, "Efficacy of Hexapeptide-7 on Menopausal Skin," Journal of Drugs in Dermatology, Strategic Communication in Dermatology, New York, NY, US, vol. 9, No. 1, Jan. 1, 2010, pp. 49-54.
Steinstraesser, Lars, et al, "Innate Defense Regulator Peptide 1018 in Wound Healing and Wound Infection," PLOS One, vol. 7, No. 8, Aug. 6, 2012, p. e39373.
Kendall, Ryan T., et al, "Fibroblasts in Fibrosis: Novel Roles and Mediators," Frontiers in Pharmacology, vol. 5, article 123, May 2014.
PCT/US2014/012378—International Preliminary Report on Patentability dated Mar. 30, 2015.

(Continued)

*Primary Examiner* — Julie Ha
(74) *Attorney, Agent, or Firm* — Thomson Law PLLC

(57) ABSTRACT

Peptides having four to six amino acid residues are disclosed that possess biological activity. These peptides constitute short fragments of the peptide HB-107 (MPKEKVFLKIEK-MGRNIRN) (SEQ ID NO: 10), which itself is a fragment of the antimicrobial protein cecropin B, and exhibit cell stimulatory and migratory properties. The inventive peptides comprise four to six contiguous amino acid residues located between position 11 and 16 of HB107 (MPKEKVFLKIEK-MGRNIRN) (SEQ ID NO: 10), namely EKMGRN (SEQ ID NO: 1). The disclosed peptides comprise a useful agent for the medical treatment of injury to the skin, such as from diabetic ulcers. The peptides also are effective in preventing and reversing skin surface damage resulting from various environmental insults. Importantly, the therapeutic effects of the peptides manifest at concentrations equal to or greater than those of peptide HB-107 (SEQ ID NO: 10), and thus represent a less expensive, more versatile means for developing effective therapies. Methods for the production and use of these peptides are also disclosed.

12 Claims, No Drawings

(56) References Cited

OTHER PUBLICATIONS

RU2015138925, "Official Action," mailed Feb. 20, 2016, 10 pages.
SG11201505538Q, "Invitation to Respond and Written Opinion," mailed Apr. 20, 2016, 8 pages.
CN201480090001.0, First Office Action, mailed Jun. 1, 2016, 16 pages.
RU2015138925, Official Action, mailed Jun. 17, 2016, 10 pages.

\* cited by examiner

SEQUENCE LISTING

```
<160> NUMBER OF SEQ ID NOS: 10

<210> SEQ ID NO 1
<211> LENGTH: 6
<212> TYPE: PRT
<213> ORGANISM: Artificial Sequence
<220> FEATURE:
<223> OTHER INFORMATION: Peptide HB2265

<400> SEQUENCE: 1

Glu Lys Met Gly Arg Asn
1               5

<210> SEQ ID NO 2
<211> LENGTH: 5
<212> TYPE: PRT
<213> ORGANISM: Artificial Sequence
<220> FEATURE:
<223> OTHER INFORMATION: Peptide HB2262

<400> SEQUENCE: 2

Lys Met Gly Arg Asn
1               5

<210> SEQ ID NO 3
<211> LENGTH: 5
<212> TYPE: PRT
<213> ORGANISM: Artificial Sequence
<220> FEATURE:
<223> OTHER INFORMATION: Peptide HB2263
```

```
<400> SEQUENCE: 3

Glu Lys Met Gly Arg
1               5

<210> SEQ ID NO 4
<211> LENGTH: 4
<212> TYPE: PRT
<213> ORGANISM: Artificial Sequence
<220> FEATURE:
<223> OTHER INFORMATION: Peptide HB2234

<400> SEQUENCE: 4

Glu Lys Met Gly
1

<210> SEQ ID NO 5
<211> LENGTH: 4
<212> TYPE: PRT
<213> ORGANISM: Artificial Sequence
<220> FEATURE:
<223> OTHER INFORMATION: Peptide HB2235

<400> SEQUENCE: 5

Met Gly Arg Asn
1

<210> SEQ ID NO 6
<211> LENGTH: 3
<212> TYPE: PRT
<213> ORGANISM: Artificial Sequence
<220> FEATURE:
<223> OTHER INFORMATION: Peptide HB2268

<400> SEQUENCE: 6

Lys Met Gly
1

<210> SEQ ID NO 7
<211> LENGTH: 3
<212> TYPE: PRT
<213> ORGANISM: Artificial Sequence
<220> FEATURE:
<223> OTHER INFORMATION: Peptide HB2269

<400> SEQUENCE: 7

Gly Arg Asn
1

<210> SEQ ID NO 8
<211> LENGTH: 4
<212> TYPE: PRT
<213> ORGANISM: Artificial Sequence
<220> FEATURE:
<223> OTHER INFORMATION: Peptide HB2232

<400> SEQUENCE: 8

Lys Ile Glu Lys
1

<210> SEQ ID NO 9
<211> LENGTH: 6
<212> TYPE: PRT
<213> ORGANISM: Artificial Sequence
<220> FEATURE:
<223> OTHER INFORMATION: Peptide HB1026

<400> SEQUENCE: 9
```

```
Gly Arg Asn Ile Arg Asn
1               5

<210> SEQ ID NO 10
<211> LENGTH: 19
<212> TYPE: PRT
<213> ORGANISM: Artificial Sequence
<220> FEATURE:
<223> OTHER INFORMATION: Peptide HB107

<400> SEQUENCE: 10

Met Pro Lys Glu Lys Val Phe Leu Lys Ile Glu Lys Met Gly Arg Asn
1               5                   10                  15

Ile Arg Asn
```

SHORT BIO-ACTIVE PEPTIDES FOR PROMOTING WOUND HEALING

This application is a Section 371, United States national stage filing of PCT/US2014/012378 filed 21 Jan. 2014, which claims the benefit of priority to U.S. Provisional Application No. 61/764,913, filed 14 Feb. 2013, each of which is herein incorporated by reference in its entirety.

FIELD OF THE INVENTION

The invention relates to peptides having biological, cosmetic and therapeutic activity. Particularly, the invention relates to short peptides having four to six contiguous amino acid residues of SEQ ID NO:1 (EKMGRN) that stimulate keratinocyte cell proliferation and migration. The invention is further related to methods of using of these peptides to promote wound repair and treat various insults affecting the skin and other related body surfaces such as the oral cavity.

BACKGROUND OF THE INVENTION

Skin is the largest organ of the body and the interface between the environment and our internal biology. It is composed of two primary layers: the epidermis, which is the outermost layer of skin; and the dermis, which lies just beneath the epidermis. Keratinocytes are the major cells, constituting 95% of the epidermis. The suprabasal keratinocytes differentiate into a chemically and physically resistant horny layer surrounded by proteins and lipids, including ceramides, cholesterol and fatty acids. Natural or forced removal of the top layers of this cornified epithelium will stimulate turnover by the underlying cells to replace the damaged or lost cells. This cornified layer provides the protective and water-barrier functions between the body and the environment. The primary function of keratinocytes is the formation of a barrier to protect the body against chemical, physical and mechanical hazards, invasion by micro-organisms, heat, UV radiation and water loss (Proksch et al., 2008). Keratinocytes are also a main constituent of mucosal tissues that are continuous with the epidermis (Presland and Dale, 2000).

A wound is defined as a break in the epithelial integrity of the skin. Normal wound healing involves a complex and dynamic but superbly orchestrated series of events including inflammation, new tissue formation and tissue remodeling. Wound healing begins the moment the tissue is injured and requires precise coordination of epithelialization and dermal repair, of which the epithelialization process is ultimately dependent on the migration, proliferation, and differentiation abilities of keratinocytes (Singer and Clark, 1999). During epithelialization, keratinocytes located at the wound perimeter migrate and proliferate to form a single layer over the wound. Further proliferation and differentiation of the keratinocytes establish an epidermal layer comprising the normal stratified layers. Also keratinocytes with normal dermal fibroblasts lead to upregulation of mRNA for collagen type I and III, increased fibroblast proliferation, and extracellular matrix accumulation and remodeling to complete healing by restoring the structure and function of the tissue (Bergers G and Coussens L M, 2000). Thus, the ability of keratinocyte proliferation and migration is essential for performing these processes on the skin surface. With the knowledge that certain growth factors are naturally engaged during wound healing, work has been directed towards developing growth factor-based methods for treating wounds (Mustoe et al., 1994; Steed, 1995). However, most attempts employing such a strategy have failed to achieve clinically significant results, due in part to difficulties associated with use of therapeutic proteins such as the large size of the proteins involved. Use of growth factor therapies also suffers from the complexity and high costs associated with preparing large proteins. Host defense peptides (HDPs), also known as antimicrobial peptides, have been implicated as regulators of cutaneous wound healing. Due to their small sizes these short active peptides have attracted the attention for therapeutics development (Zhang and Falla, 2006).

HDPs are ubiquitous in nature and form central components of the innate immune system of eukaryotes. They are essential to innate host defense as effectors of pathogen clearance as well as modulation of host cell behaviors to promote tissue regeneration and repair. Normal wound repair involves a precise orchestration of inflammation, epithelialization, tissue-granulation and remodeling. Host defense peptides have been shown to influence all of these behaviors. The cathelicidin PR-39 possesses anti-inflammatory function by inhibiting neutrophil oxidase activity, and induces syndecans, heparin sulfate proteoglycans important in wound repair (Gallo et al., 1994; Shi J., Ross, C R. et al., 1996). Another member of the cathelicidin family host defense peptides, LL-37, was also shown to influence the reepithelialization of human skin wounds in organ culture (Heilborn J D, et al., 2003). Human neutrophil defensin promotes the expression of type I collagen while inhibiting the expression of interstitial collagenase (Oono T., et al., 2002). Furthermore, human cathelicidin LL-37 and human β-defensin-3, which are extremely diverse, promote activities including the stimulation of epithelial cell migration, promotion of angiogenesis, and suppression of pro-inflammatory responses (Steinstraesser et al., 2008, 2009). They attract neutrophils, monocytes, mast cells, and T lymphocytes, and also induce the production of neutrophil and monocyte chemoattractants in many cell types. Recently, HDPs have also been implicated as regulators of cutaneous wound repair by modulating inflammation, angiogenesis, and extracellular tissue deposition and remodeling. It has been shown that the influence of HDPs on wound repair is not dependent on antimicrobial function and provides a potential novel clinical application for HDPs. We have previously reported that a non-antimicrobial host defense peptide HB107 (MPKEKVFLKIEKMGRNIRN) (SEQ ID NO.: 10) derived from cecropin B retained the ability to aid in wound repair in a murine model and the benefit observed with HB107 was indistinguishable from the wound treated with growth factor rhPDGF (Lee, et al., 2004). Histological analysis of HB107 treated wounds suggests that epidermal hyperplasia was increased in HB107-treated wounds, an indication that HB107 may influence keratinocyte proliferation or migration (Lee P H., et al., 2004). A new group of synthetic variants of HDPs, termed innate defense regulators (IDRs), which provide broad-spectrum protection against systemic infections with multidrug-resistant bacteria, have recently been described (Easton D M., et al., 2009). For example, IDR-1 and IDR 1002 confer protection against microbial challenges by enhancing innate immune defenses of the host while suppressing potentially harmful excessive inflammatory responses (Easton et al., 2009; Nijnik A., et al., 2010).

SUMMARY OF THE INVENTION

The present invention relates to short bio-active peptides that are useful for promoting wound healing in mammals. The wounds preferably targeted by the isolated peptides are those affecting the skin and associated mucosal surfaces. Though not to be limited to any particular mechanism, the inventive peptides are able to affect wound healing by stimulating cell proliferation and migration. The inventive peptides are useful in both in vitro and in vivo manners, and are able to induce the aforementioned activities in keratinocytes.

One embodiment of the present invention is drawn toward isolated peptides that contain four to six contiguous amino acid residues located between position 11 and 16 of HB107 (MPKEKVFLKIEKMGRNIRN) (SEQ ID NO: 10), namely EKMGRN (SEQ ID NO:1). The isolated peptides may contain either L- or D-enantiomeric forms of amino acids, or combination thereof. According to yet another embodiment of the invention, the isolated peptides may be conjugated to a carrier protein, or modified via C-terminal amidation or N-terminal acetylation with fatty acids (i.e. lipidation). These additions enhance the bio-activity of the peptides when applied to skin and wounds thereof.

According to certain preferred embodiments of the current invention, the isolated peptides all contain a methionine. Specific embodiments of the isolated peptides comprise SEQ ID NO: 1, 2, 3, 4 and 5 all of which show stimulatory activities towards cell proliferation and migration and affect wound repair.

| SEQ ID NO. | HB NO. | Sequence |
| --- | --- | --- |
| 1 | HB2265 | EKMGRN |
| 2 | HB2262 | KMGRN |
| 3 | HB2263 | EKMGR |
| 4 | HB2234 | EKMG |
| 5 | HB2235 | MGRN |

Another embodiment of the present invention is drawn toward the manufacture of a medicament for therapeutic or cosmetic compositions which contain a pharmaceutically or cosmetically acceptable carrier and one or more of the aforementioned peptides. The aforementioned compositions are useful for medicament or cosmetic application for healing skin wounds of mammals. The peptide in such compositions preferably ranges in concentration from about 0.1 µg/mL to about 500 µg/mL, or from about 0.1 µg/mL to about 20 mg/mL. Preferred forms of the composition are aerosols, emulsions, liquids, solutions, lotions, creams, pastes, ointments, powders, gels and foams.

Additionally, the peptides of the present invention, and compositions containing them, may provide useful features for inclusion in general skin care and cosmetic formulations, such as various skin cosmetics, skin creams, lotions, sunscreens, and therapeutic lotions or creams such as anti-acne formulations for post laser procedure care.

The present invention is also directed towards methods of using the aforementioned compositions for healing wounds in mammals. Typically, the treatment method entails administering an effective amount of peptide-containing compositions to wounds, especially those of the skin (epidermis) and associated mucosal tissues, for an effective amount of time. Such wounds include surgical wounds, abrasions, blisters, burns, lacerations, ulcers, bruises, rashes, scars, stretch marks and skin damage due to intrinsic and extrinsic effects of aging and environmental exposure, including wrinkling, skin sagging and photo-damage.

DETAILED DESCRIPTION OF THE INVENTION

U.S. Pat. Nos. 5,962,410, 5,861,478, and 7,696,174 provide disclosures useful for understanding the present invention and are herein incorporated by reference in their entirety. Peptide HB107 (MPKEKVFLKIEKMGRNIRN) (SEQ ID NO: 10) itself constitutes a fragment of cecropin B, which is an antimicrobial protein present in a species of moth. Although HB-107 does not display the bacteriostatic effects of the protein from which it is derived, it does display epidermal wound healing qualities (Lee et al., 2004). This 19 amino acid residue peptide is a multi-functional immune-modulator that stimulates keratinocyte proliferation, migration, scratch wound closure and anti-inflammatory activities that are essential for wound healing.

Based on this rationale we focused on a six amino acid stretch represented by SEQ ID NO: 1 (HB2265), EKMGRN, of HB107 from position of 11-16 in the current study. Schematic illustration of peptides comprising of 4 to 6 contiguous amino acid residues located in HB107

| SEQ ID NO. | HB NO. | Sequence |
| --- | --- | --- |
| 10. | HB107 | MPKEKVFLKIEKMGRNIRN |
| 1. | HB2265 | EKMGRN |
| 2. | HB2262 | KMGRN |
| 3. | HB2263 | EKMGR |
| 4. | HB2234 | EKMG |
| 5. | HB2235 | MGRN |
| 6. | HB2268 | KMG |
| 7. | HB2269 | GRN |
| 8. | HB2232 | KIEK |
| 9. | HB1062 | GRNIRN |

We further generated peptides comprising of 3 to 5 contiguous amino acid residues from SEQ ID NO: 1, represented by SEQ ID NOs: 2, 3, 4, 5, 6, 7, 8 and 9. To assess whether the newly derived peptides possess wound healing activity, the peptides SEQ ID NOs 1, 2, 3, 4, 5, 6, 7, 8 and 9 were subjected to keratinocyte scratch wound test, an assay well accepted for assessing the ability of active compound to promote wound closure. It is shown in Table 1 that the peptides of SEQ ID NOs 1, 2, 3, 4, and 5 significantly induce the scratch wound closure at concentration between 10 and 20 µg/ml. The percentage of wound closure induced by SEQ ID NOs: 1, 2, 3, 4, and 5 was ranging from 182-218% compared to that of PBS treated which was taken as 100%. However the tripeptides represented by SEQ ID NO: 6 (HB2268) and SEQ ID NO: 7 (HB2269), and the tetrapeptide HB2232 (SEQ ID NO: 8), all failed to induce scratch wound closure (Table 1). Another peptide SEQ ID NO: 9 (HB1062) (GRNIRN) which lacks the amino acid methionine residue was also shown unable to promote scratch wound closure in the same in vitro keratinocyte scratch wound test (Table 1). Therefore, there are two crucial elements required for the observed wound healing activity. First, must be a minimal of four contiguous amino acid residues; and second, must contain a methionine residue in the designated sequences. The fact that both HB2232 (KIEK) (SEQ ID NO: 8) and HB1062 (GRNIRN) (SEQ ID NO: 9) are inactive to promote scratch wound closure suggests that the methionine residue is an irreplaceable amino acid that must be present as one of the amino acids in the four or more contiguous residues to promote wound healing activity. We thus conclude that four to six contiguous amino acid residues, which must contain a methionine residue, located in the center region of HB107 (SEQ ID NO: 10) from position of 11 to 16 within EKMGRN (SEQ ID NO: 1), promote wound repair. To confirm that the activity was not due to toxicity of peptides towards keratinocyte, all peptides were subjected to the MTT cytotoxicity test. None of the peptides tested were cytotoxic to normal skin keratinocyte in vitro at concentrations up to 500 µg/ml (Table 1).

The observed activity on scratch wound closure in vitro is closely correlated to the proliferation activity of the peptides as shown in the in vitro keratinocyte proliferation assay (Table 2). The proliferative activity is more profound at lower concentrations. The optimal concentration required to stimulate keratinocyte proliferative activity for each peptide varies but generally within a range from 0.625 to 5 µg/ml (Table 2). SEQ ID NO 1 (HB2265) shows the activity at 2.5 and 5 µg/ml and SEQ ID NO 2 (HB2262) stimulates keratinocyte proliferation at all concentrations tested from 0.625 to 5 µg/ml. SEQ ID NO: 3 (HB2263), SEQ ID NO: 4 (HB2234), and SEQ ID NO: 5 (HB2235) confer such activity at relatively lower concentrations from 0.625 to 2.5 µg/ml. The tripeptides HB2268 (KMG) (SEQ ID NO: 6) and HB2269 (GRN) (SEQ ID NO: 7) do not seem to show proliferation activity at all concentrations tested. Also the tetrapeptide HB2232 (SEQ ID NO: 8) does not induce keratinocyte proliferation (Table 2). In conclusion the peptides of the current invention possess modulating activity towards skin keratinocyte proliferation and such activity is essential for cutaneous wound repair.

To better understanding the mechanism we put one representative peptide, SEQ ID NO: 5 HB2235, to a gene profiling study performed by SUNNY BIODISCOVERY™ gene profiling (Santa Paula, Calif.) using EPIDERM™ tissue substitutes (MatTek, Ashland Mass.). The skin substitutes were equilibrated for overnight then full thickness puncture wounds were applied with 20G needle prior to treatment with peptide or water control in duplicates for 24 hr. A set of two normal tissues was also used as control to see gene profiling change between wounded and normal tissues. At the end of treatment RNA was extracted and subjected to PCR array analysis. The first comparison was made between wounded non-treated vs. non-wounded non-treated tissues to see the expression profile of genes in response to injury, then a comparison between wounded non-treated vs. wounded treated with HB2235 (SEQ ID NO: 5) was made. Table 3 lists some genes that are significantly affected among different signaling pathways of the wound healing cascade. The affected genes represent those encoding for matrix proteins such as collagens and integrins, genes in the proinflammatory cascade such as cytokines and chemokine receptors, genes involved in tissue remodeling process such as matrix metalloproteinases, plasminogen activators and protease inhibitors, and others that are involved in wound healing. Successful wound healing is a well-orchestrated process involving many cell types, non-cellular components, such as fibrin and collagen, and a cocktail of biologically active chemical species. Although it is a continuous cascade of overlapping processes, it is often divided into three phases: inflammation; proliferation; and remodeling. As shown in Table 3, after acute wounding or injury compared to normal non-wounded skin tissue, there is significant up-regulation of genes that are normally associated with proinflammatory cytokines and chemokine receptors. For example, C-X-C chemokine ligands 2 and 5 were up 4.29 and 2.93 fold, respectively (Table 3). Granulocyte macrophage colony stimulating factor 2 and interleukin-6 signal transducer are also up 1.87 and 1.93 fold, respectively. During the inflammatory phase, platelet aggregation at the injury site is followed by infiltration of leukocytes such as neutrophils and macrophages into the wound site during which a fibrin-rich clot is formed to prevent further blood loss and acts as a scaffold for early cell migration into the wound. The inflammatory signals observed 24 hr post injury (wounded vs. normal tissues) are consistent and essential to attract neutrophils and macrophages to the site of injury in physiological condition. The fibrin-rich clot is eventually broken down in a later stage by proteins such as plasmins. The production of plasmin is governed by the presence of tissue plasminogen activator, a protein that converts plasminogen to plasmin in close connection with the function of matrix metalloproteinases (MMPs). This is clearly seen in Table 3 that there is up regulation of genes encoding both tissue and urokinase plasminogen activators (PLAT and PLAU) as well as MMPs (MMP-1) 24 hr post injury. In the normal wound healing process the remodeling stage occurs on a longer time scale, often taking weeks to complete which involve a phase of rapid proliferation of keratinocytes and fibroblasts that synthesize and remodel collagens. In close examination of HB2235 (SEQ ID NO: 5) treated wounded tissues, we observed that there are several crucial steps in the wound healing cascade that are being influenced or modulated by HB2235 (SEQ ID NO: 5). Firstly, the peptide clearly shortens the duration of initial inflammatory phase as indicated by that the genes encoding proinflammatory cytokines and chemokine receptors were significantly down regulated after 24 hr treatment with HB2235 (SEQ ID NO: 5) (Table 3). In consistent with down regulation of inflammatory signals, the anti-inflammatory cytokine, IL-10, is up regulated (Table 3). This is significant as numerous studies indicate that reducing the length or duration of the inflammation process can significantly facilitate wound healing as it was evident that delayed wound healing was associated with profound inflammation throughout all stages of wound healing (Leitch et al., 2009; Wang et al., 2006). Secondly, HB2235 (SEQ ID NO: 5) significantly down regulate genes encoding for plasminogen activators and MMPs after 24 hr treatment indicating that it may accelerate tissue granulation process. Thirdly, by modulating genes encoding for growth factors such as TGF-β 1, PDGF, EGF that are essential for cell migration and proliferation activities the peptide is clearly involved in acceleration of re-epithelialization and tissue remodeling process during which newly formed tissues begin to cover the wound area to complete tissue repair. Most significantly HB2235 (SEQ ID NO: 5) treated tissues showed more than 5-fold upregulation of the vitronectin (VTN) (Table 3). VTN is an abundant glycoprotein found in extracellular matrix and well known to promote keratinocyte adhesion, proliferation and migration (Upton et al., 2008). Fourthly, in consistent with cell proliferation and migration activity, HB2235 (SEQ ID NO: 5) stimulates up regulation of genes encoding for matrix proteins such as collagens and integrins that are essential for re-epithelialization and tissue remodeling (Table 3). The gene array analysis strongly supports that the peptide accelerates epithelialization process by promoting cell proliferation and migration as well as matrix remodeling and collagen stimulation.

The peptides of the present invention, including SEQ ID NOs 1, 2, 3, 4 and 5, display activities that are important for up regulation of keratinocytes migration and proliferation that are essential for wound healing processes in epidermal tissues where keratinocytes reside. The peptides disclosed in the current invention are novel and shorter than previously disclosed sequences. The biological activities elicited by the peptides of the current invention are cell proliferation and migration both of which play a large role in mediating the wound healing function.

Because of the smaller size, the peptides, for example, having four amino acid residues of the current invention are easier and thus significantly cost effective to manufacture. Also, in contrast to larger peptides, the disclosed peptides are easier to be manipulated for chemical modifications and less solubility issues. Their easy-of-handing enables a greater number of drug delivery options, such as the vehicle to be used and how it is applied. The small size and greater solubility of the inventive peptides permit their increased healing potency through increased absorption and retention at the wound site; local keratinocytes and other cells that are exposed to higher concentrations of the peptides for longer period of time.

All the peptides disclosed may be synthesized using standard Fmoc (9-fluorenylmethoxycarbonyl) solid-phase chemistry. Each of the above-described peptides may comprise L- or D-amino acid enantiomers. The carboxy-terminus of the peptides can be acidic (—COOH) or be amidated (e.g., —CONH2, —CONHR, or —CONR2). Amidation of the carboxy-terminus may render the inventive peptides less susceptible to protease degradation and increase their polarity compared to the free acid forms, therefore providing heightened therapeutic potency. It is discussed that N-terminus lipidation or acetylation may improve peptide penetration across skin without altering the bioactive function of the peptide (Samah A, 2011). Therefore the peptides may also be lipidated which may provide for enhanced skin penetration. Examples of saturated or unsaturated fatty acids that can be used to provide the $C_{12-18}$ lipid—component of the compounds of the invention include lauric acid, myristic acid, palmitic acid, stearic acid, myristoleic acid, palmitoleic acid, oleic acid and linoleic acid.

Peptides may be conjugated to soluble or insoluble carrier molecules to modify their solubility properties as needed and to increase the local concentrations of peptides in targeted tissues. Examples of soluble carrier molecules include polymers of polyethyleglycol (PEG) and polyvinylpyrrolidone; examples of insoluble polymers include but not limited to silicates, polystyrene and cellulose. Peptides may be micro-encapsulated using liposome technology or via nano-technology to enhance their stability and for controlled release to enhance their stability during and after application.

The current invention is directed towards methods of using the above described peptides, such as in formulations or as therapeutic agents. These methods may involve the use of a single peptide, or multiple peptides in combination. In certain instances, the inventive composition can be disposed within devices placed upon, in, or under the skin. Such devices include transdermal patches, implants, and injections which release the substances in such a manner as to contact the skin or hair follicle either by passive or active release mechanisms. The compositions used to deliver the peptides in the methods described herein can be in the form of an aerosol, emulsion, liquid, lotion, solution, gel, micro-encapsulation, cream, paste, ointment, powder, foam, or other pharmaceutically acceptable formulation. Furthermore, the peptides can be delivered using less involved formulations such as deionized/distilled water, PBS or standard medical saline solutions.

The formulation may optionally have cosmetic appeal, and/or contain other agents such as retinoids, vitamin C or other peptides that can act as adjuvant for the therapeutic action of the inventive peptides. Antibiotics can also be added to the formulation in order to ward off infection, thereby permitting maximal healing processes to occur.

The formulation may contain protease inhibitors. A protease inhibitor can be selected to specifically target proteases that would be expected to degrade the selected bioactive peptide; such a selection would be determined based on the length and/or sequence of the bioactive peptide. However, protease inhibitors need not necessarily be selected in any specific manner; for example, a protease inhibitor cocktail, which contains two or more inhibitors, can be employed in the instant invention. The following types of protease inhibitors can be incorporated in the invention: serine protease inhibitors, cysteine protease inhibitors, aspartate protease inhibitors, metalloproteinase inhibitors, thiol protease inhibitors and threonine protease inhibitors. The protease inhibitor used in the invention may be a peptide or protein or chemicals. Non-limiting examples of such inhibitors are the serpins, which include alpha-1-antitrypsin, complement 1-inhibitor, antithrombin, alpha-1-antichymotrypsin, plasminogen activator inhibitor 1, and neuroserpin, or chemicals including, but not limited to, ursolic acid and tranexamic acid that can act as adjuvant for the therapeutic action of the inventive peptides.

The peptides of the current invention may be used for treating wounds of the skin. Skin epidermis consists of a highly dynamic stratified epithelium made principally from keratinocytes. Other cell types such as fibroblasts also populate the epidermis. New differentiating keratinocytes continuously emerge from the proliferative basal layer of the epidermis to replenish the upper layers, progressively differentiating into the external cornified and desquamating dead envelope. Keratinocytes are also a main constituent of mucosal tissues that are continuous with the epidermis (Presland and Dale, 2000). Such tissue lacks the impermeable, cornified layer of the epidermis, and forms the inner-lining surfaces associated with the mouth, nose, throat, ear, anus and genitalia. Similar to the skin, mucosal surfaces are important for preventing entry of infectious agents into various tissues of the body, thus, injury to these tissue types may compromise the health of an individual. Skin and mucosal tissue damage occurs when the epidermal layer is breached, such as from a laceration, burn or blister. Injury can also involve crushing or bruising, which involves tissue damage without concurrent fissure of the epidermis. Skin infections as well as certain chronic illnesses such as cancer and autoimmune diseases can also exact a toll on epidermal surfaces. Ulcers such as those affecting diabetics or those associated with pressure sores are another form of skin damage; these wounds are often quite intractable, being inflamed, prone to infection, and requiring a lengthy healing process. The persistence of an ulcer or other type of chronic wounds is due to a failure of cellular processes involved in healing. The failure in wound healing may be a result of inability to epithelialize the lesion partially due to the fact that the keratinocytes at the wound border do not migrate to close or cover the sore (Enoch and Price, 2004). Healing of skin and mucosal wounds is orchestrated, in part, through the activation of basal keratinocytes. Upon activation the keratinocyte located at the wound perimeter proliferate and migrate to form a single layer over the wound in a process referred to as epithelialization. Further proliferation and differentiation of the keratinocytes establishes an epidermal layer comprising the normal stratified layers (Enoch and Price, 2004). Therefore, the current invention may also be used to treat damages associated with keratinocytes in mucosal tissues. The term "associated mucosal tissues" relates to any tissue organized in a manner similar to the skin and contains epithelial cells/keratinocytes. Examples of such tissues are oral, nasopharyngeal, aural and urogenital surfaces, as well as the palpebral conjunctive of the eye. Examples of wounds or lesions/injuries that can affect these tissues and are amenable to treatment with the inventive peptides are abrasions, blisters, burns, lacerations, punctures, ulcers, bruises, rashes and scars. Post-surgical trauma can also be treated with the peptides.

Another form of epidermal damage is subtle and results over a long period of time, eventually compromising skin function, so called aging skin. Aging skin is affected by a genetic program as well as by cumulative environmental and endogenous insults that take place throughout the individual's life span. There are two main processes that induce skin aging; intrinsic (chronological aging) in sun protected skin and extrinsic (photo-aging) in sun-exposed areas. Intrinsic aging reflects the genetic background and depends on time. Regardless, aging skin shares with one or more of the following: wrinkles, fine lines, hyperpigmentation, loss of radiance, smoothness, firmness, skin tone clarity and evenness, and alterations in pore appearance. Underlying these visible signs are various histological and cytological changes induced by acute or chronic exposure of environmental stimuli such as ultraviolet (UV) and pollutions in addition to genetic predisposition. Cosmetic problems such as wrinkling, dryness, thinning, sagging, greater susceptibility to bruising and sunburns are usual outward signs of epidermal damage that, in addition to aging, may also occur prematurely due to prolonged exposure to damaging agents such as ultraviolet rays and pollutions. Research suggests that the most noticed morphological modification of skin aging is the progressive loss of skin tissue. This loss of skin tissue can be attributed to several factors such as loss of cells and decreased cell proliferation. In self-renewing tissue like the epidermis, cell numbers are tightly regulated by a delicate balance between proliferation, terminal differentiation and apoptosis (Robert L, Labat-Robert J and Robert A M. 2009). Therefore the disclosed peptides may be used towards problems associated with aging skin caused by both intrinsic and extrinsic stimuli, to prevent or reverse the effects of aging. In a related manner, the peptides could be applied to tissue that had been damaged by exposure to various external agents such as sunlight. The invention can also be used as a cosmetic in these regards to render skin a more youthful appearance and texture, and to provide better function. The short peptides by themselves unaltered, or via chemical modification and/or specialized delivery, can be made to penetrate through the epidermis to affect processes counter to those that cause skin thinning, wrinkles, fragility and roughening/hardening. As the keratinocytes are the main component of epidermal surfaces and are diminished in aged and damaged skin, replenishment thereof by peptide stimulation is expected to reverse the aforementioned problem.

Skin is relatively elastic, but there are limits to its capacity to stretch. Stretch marks, or striae, are a form of scarring on the skin with an off-color hue. They are caused by tearing of the dermis, which over time may diminish, but will not disappear completely. They first appear as reddish or purple lines, but tend to gradually fade to a lighter range. Stretch marks are often the result of the rapid stretching of the skin associated with rapid growth or rapid loss of weight. Stretch marks can appear anywhere on body sites that do not undergo notable or excessive stretching or distention at all. Most common places are the abdomen, breasts, upper arms, underarms, back, thighs, hips, and buttocks. The stretch marks are often caused by the hormonal changes of some major stages of life like puberty and pregnancy, but corticosteroid treatment, obesity, aesthetic surgery and intensive body building may lead to stretch marks. Under the action of corticosteroids the growth of both keratinocytes and fibroblasts can be severely damaged and consequently the synthesis of collagens I and III as well as fibronectin synthesis is also significantly reduced up to over 90% compared to normal skin (Rogalski et al., 2002). Repair and restore the function of keratinocytes in the dermal/epidermal section could be the key to stretch mark correction. The peptides of the current invention are promoting keratinocyte proliferation and migration and are therefore ideal for treatment of stretch marks.

Generally, a pharmaceutically acceptable formulation would include any carrier suitable for use on human skin. Such pharmaceutically and cosmetically acceptable carriers include ethanol, dimethyl sulfoxide, glycerol, silica, alumina, starch, and equivalent carriers and diluents. The formulation may optionally have cosmetic appeal, and/or contain other agents such as retinoids or other peptides that can act as adjuvants for the therapeutic action of the inventive peptides. Antibiotics can also be added to the formulation in order to ward off infection, thereby permitting maximal healing processes to occur. The concentration of the peptide in the composition can be about 0.1 µg/mL to about 500 µg/mL or about 0.1 µg/mL to about 20 mg/mL; however, the ultimate concentration employed may vary outside these ranges, depending on the nature of the wound/tissue condition, the bio-activity of the inventive peptide and the use of any adjuvant or technique to obtain enhanced composition absorption.

In a preferred embodiment of the instant invention, where the composition is to be in contact with human keratinous tissue, any additional components besides the inventive peptides should be suitable for application to keratinous tissue; that is, when incorporated into the composition, such other components demonstrate undue toxicity, incompatibility, instability, allergic response, and the like within the scope of sound medical judgment. The CTFA Cosmetic Ingredient Handbook, Second Edition (1992) describes a wide variety of non-limiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g. clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, cosmetic biocides, denaturants, drug astringents, external analgesics, film formers or materials, opacifying agents, pH adjusters, propellants, reducing agents, sequestrants, skin bleaching and lightening agents (e.g. hydroquinone, kojic acid, ascorbic acid, magnesium ascorbyl phosphate, ascorbyl glucosamine), skin-conditioning agents (e.g. humectants), skin soothing and/or healing agents (e.g. panthenol and its derivatives, aloe vera, pantothenic acid and its derivatives, allantoin, bisabolol, and dipotassium glycyrrhizinate), skin treating agents, thickeners, and vitamins and derivatives thereof.

The administration of the inventive peptides and associated compositions may be made to humans and animals, including all mammals. Application may also be made in combination with typical and/or experimental materials such as tissue grafts, skin substitutes, tissue culture products and dressings. Examples include, but not limited to, gauzes (woven and non-woven, impregnated, nonadherent, packing, debriding); compression bandages and system; wound fillers and cleansers; contact layers; collagens; amniotic membranes; acellular human dermis; acellular matrices and combination products; and various commonly used dressings.

| List of commonly used dressings | |
|---|---|
| Categories of Wound Dressings | Products |
| Films | BIOCLUSIVE ™ (Johnson & Johnson Medical, Inc) |
| | OMIDERM ™ (omicron Scientific Ltd.), |
| | OPSITE* (Smith & Nephew United, Inc) |
| | POLYSKIN ®II transparent dressing (Kendall Healthcare) |
| | TEGADERM ™ (3M Health Care) |
| Hydrogels | INTRASITE ™ (Smith & Nephew United, Inc), |
| | NU-GEL ™ (Johnson & Johnson Medical, Inc.) |
| | VIGILON ® (Bard Medical Division) |
| Hydrocolloids | COMFEEL ® (Coloplast Sween Corp.) |
| | DUODERM ® (ConvaTec ®) |
| | RESTORE ™ (Hollister Incorporated) |
| Polysaccharides | BARD ABSORPTION DRESSING* (Bard Medical Division) |
| | DEBRISAN (Johnson & Johnson Medical, Inc.) |
| | DUODERM ® Granules (ConvaTec ®) |
| Alginates | KALTOSTAT ® (ConvaTec ®) |
| | SORBSAN ™ (Dow Hicham Pharmaceuticals Inc) |
| Foam Dressings | ALLEVYN* (Smith & Nephew United, Inc) |
| | LYOFOAM ® (Acme United Corporation) |
| Laminates | BIOBRANE ® (Dow Hickam Pharmaceuticals Inc) |

*Asterisks refer to individual company trademarks

In general, the composition can be administered topically, orally, transdermally, systemically, or by any other method known to those of skill in the art to be useful to deliver the inventive peptides to the target tissue. Compositions may also be applied in an in vitro or ex vivo manner, either to cells or patient grafts growing in culture, for example.

The compositions of the present invention can contain one or more additional agents that exert skin care activity. Beside the bioactive peptide component, the instant invention can contain other active agents such as hyaluronic acid, niacinamide, phytantriol, farnesol, bisabolol, salicylic acid, retinol, retinoic acid, alphahydroxy acids, ascorbic acid and alguronic acid. It is expected that certain additional active agents will act synergistically with the bioactive peptide component, or will enhance the shelf-life of the formulation.

Further, the abbreviations for the amino acids follow conventional usage:

| | | |
|---|---|---|
| Alanine | Ala | A |
| Arginine | Arg | R |
| Asparagine | ASN | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Details on techniques for formulation and administration of pharmaceuticals may be found in the latest edition of Remington's Pharmaceutical Sciences (Mack Publishing Co, Easton Pa.). Although local topical delivery is desirable, there are other means of delivery, for example: oral, parenteral, aerosol, intramuscular, subcutaneous, transcutaneous, intramedullary, intrathecal, intraventricular, intravenous, intraperitoneal, or intranasal administration. The present invention can be formulated in a number of carrier vehicles, for example, in a spray; an aerosol; water and an oil-type emulsion; an oil and water-type emulsion; a face cream or body cream; a sun lotion or after-sun lotion; or other topical administration vehicle. Additionally, the peptides of the present invention, and compositions containing them, may provide useful features for inclusion in general skin care and cosmetic formulations, such as various skin cosmetics, skin creams, lotions, sunscreens, and therapeutic lotions or creams such as anti-acne formulations.

The following examples are included to demonstrate certain preferred embodiments of the invention.

EXAMPLES

Example 1

Identification of Peptides that Stimulate Cell Migration and Scratch Wound Closure Human skin keratinocytes (ATCC CRL-2404) were grown in serum-free keratinocyte growth media supplemented with 5 ng/ml human recombinant epithelial growth factor (EGF) (Life Technologies Corporation, Grand Island, N.Y.). The cells were seeded onto 12-well plates and allowed to reach 100% confluent. The cell monolayer was starved for 24 hrs then a scratch wound is made using a P200 (200 µl) pipette tip. The scratch wounds are washed and photographed at time 0. Peptide was added at final concentration of 40 µg/ml. Cells are kept in an incubator at 37° C., 5% $CO_2$ incubator with >90% humidity, except when images are being captured for a short period at room temperature. Scratch wound closure is followed after 7-8 hr treatment and the results are shown in Table 1.

TABLE 1

Scratch wound closure on cultured keratinocytes. After 7 hr treatment wound closure in PBS treated was taken as 100%, wound closure in peptide treated was calculated as relative to PBS treated.

| SEQ ID NO. | HB NO. | Sequence | Wound closure after 7 hr treatment (%) | Cytotoxicity to keratinocytes (µg/ml) |
|---|---|---|---|---|
| NA | NA | PBS | 100 | — |
| 1 | HB2265 | EKMGRN | 199* | >500 |

TABLE 1-continued

Scratch wound closure on cultured keratinocytes.
After 7 hr treatment wound closure in PBS treated
was taken as 100%, wound closure in peptide
treated was calculated as relative to PBS treated.

| SEQ ID NO. | HB NO. | Sequence | Wound closure after 7 hr treatment (%) | Cytotoxicity to keratinocytes (µg/ml) |
|---|---|---|---|---|
| 2 | HB2234 | EKMG | 191* | >500 |
| 3 | HB2235 | MGRN | 218* | >500 |
| 4 | HB2262 | KMGRN | 182* | >500 |
| 5 | HB2263 | EKMGR | 188* | >500 |
| 6 | HB2268 | KMG | 107 | >500 |
| 7 | HB2269 | GRN | 102 | >500 |
| 8 | HB2232 | KIEK | 100 | >500 |
| 9 | HB1062 | GRNIRN | 99 | >500 |

*: significant

Example 2

Cytotoxicity on Normal Human Skin Keratinocytes

To make sure the peptides are not cytotoxic to the cells, normal human epidermal keratinocytes were seeded to a 96-well plate. The plate was incubated at 37° C. in the presence of 5% $CO_2$ to allow the cells to grow to >95% confluent. Peptides are diluted into stock solutions at concentrations of 50, 100, 200, and 500 µg/ml. The cell culture media are replaced with fresh media containing peptides at various concentrations then incubated at 37° C. and 5% $CO_2$ for 24 hr. At the end of treatment the cell viability was measured using MTT assay kit purchased from ATCC (Manassas Va.). The results are shown in Table 1. At the concentrations from 50 to 500 µg/ml the peptides do not changed cell viability as measured using MTT assay.

Example 3

Identification of Peptides that Stimulate Cell Proliferation

Normal human skin keratinocytes (ATCC CRL-2404) were grown in serum-free keratinocyte growth media supplemented with 5 ng/ml human recombinant epithelial growth factor (EGF) (Life Technologies Corporation, Grand Island, N.Y.). The cells are examined microscopically daily. As the culture becomes 50-75% confluent, the media in the plate is aspirated and 0.25% trypsin/EDTA is added. When the cells become rounded and detached, the trypsin is neutralized by addition of fresh culture medium. Cells are then centrifuged and the pellet is resuspended in fresh culture medium. A hemacytometer is used to count the cell suspension and the total number of cells is adjusted to about 500-1000 cells per well by adding 100 µl of cell suspension to each well. Typically, the central 60 wells are used and the outer wells are filled with fresh medium to minimize evaporation. When cells attached in each well after 6-8 hr incubation, 100 µl of fresh media containing PBS or 2× the desired concentrations of peptide is added in triplicates. The microplate is then incubated at 37° C. and 5% $CO_2$ for 48-72 hr.

At the end of incubation cells are subjected to CYTOSCAN™ SRB cell cytotoxicity assay (GBiosciences Company, St. Louis, Mo.) according to manufacturer's instructions. Briefly, cells are fixed prior to suforhodamine B (SRB) staining. After extensive washing the color is solubilized using solubilization buffer. The absorbance was measured at 565 nm with a microplate reader. The results shown in Table 2 are the mean value of triplicate treatment and values over 120 are considered significant.

TABLE 2

Modulation of normal human epidermal keratinocyte proliferation by the inventive peptides.

| | | | Concentration of peptide | | | | | | |
|---|---|---|---|---|---|---|---|---|---|
| | | | 5 µg/ml | | 2.5 µg/ml | | 1.25 µg/ml | | 0.625 µg/ml | |
| SEQ ID | HB # | Seq. | OD565 | % to PBS | OD565 | % to PBS | OD565 | % to PBS | OD565 | % to PBS |
| — | PBS | PBS | 0.1123 | 100 | 0.1123 | 100 | 0.1123 | 100 | 0.1123 | 100 |
| 1 | HB2265 | EKMGRN | 0.142 | 126* | 0.153 | 136* | 0.127 | 113 | 0.125 | 111 |
| 2 | HB2234 | EKMG | 0.103 | 92 | 0.143 | 127* | 0.149 | 133* | 0.151 | 134* |
| 3 | HB2235 | MGRN | 0.126 | 112 | 0.148 | 132* | 0.145 | 129* | 0.148 | 132* |
| 4 | HB2262 | KMGRN | 0.156 | 139* | 0.169 | 150* | 0.159 | 142* | 0.159 | 142* |
| 5 | HB2263 | EKMGR | 0.129 | 115 | 0.154 | 137* | 0.16 | 142* | 0.137 | 122* |
| 6 | HB2268 | KMG | 0.108 | 96 | 0.134 | 119 | 0.113 | 101 | 0.103 | 92 |
| 7 | HB2269 | GRN | 0.121 | 108 | 0.114 | 102 | 0.099 | 88 | 0.104 | 93 |
| 8 | HB2232 | KIEK | 0.102 | 91 | 0.126 | 112 | 0.109 | 97 | 0.115 | 102 |

*: significant

Example 4

Gene Profiling Analysis

The 84 genes encoding wound healing, extracellular matrix and adhesion molecules were analyzed using PCR arrays conducted by Sunny Biodiscovery, Inc (Santa Paula, Calif.). Briefly, EPIDERM™ skin substitutes were obtained from MatTek (Ashland, Mass.) and were handled according to the manufacturer's instructions. After overnight equilibration, the medium was changed and 10 full thickness puncture wounds were made with 20G needle and HB2235 (SEQ ID NO: 5) (330 µg/ml) or water controls were applied atop of the skin tissue in duplicate and allowed the treatment for 24 hours. A set of two normal non-wounded tissues was used also as control to see gene profiling between wounded and normal tissues. At the end of treatment tissues were collected and preserved in RNAlater solution (Ambion, Austin, Tex.). RNA was extracted and purified with Illustra mini RNAspin kit (GE Healthcare, Piscataway, N.J.). Purified total RNA was assessed at 260 nm and 280 nm with Agilent HP-8452A diode array spectrophotometer. The concentration of RNA was equalized across the samples and the expression of genes of interest was measured by real-time quantitative PCR with BioRad iCycler iQ Detection System using PCR arrays PAHS-121A, with $1^{st}$ strand synthesis kit. SYBR Green master mix and PCR running conditions from Qiagen. Efficiency ΔΔCt method was used for quantification of results, after the normalization of gene expression to 5 housekeeping genes carried with the RT2 Profiler PCR Array Data analysis version 3.5 software. Genes were considered differentially expressed if the level of expression was reasonably high (less than 30 cycles to detect) and the modulation was 1.5 or more in each duplicate series.

TABLE 3

Selected gene expression profiling on wounded skin tissue compared to non-wounded control and wounded treated with HB2235 vs. wounded non-treated, represented as fold change

| | | Fold change Up (+) or Down (−) regulation | |
|---|---|---|---|
| Symbol | Name of gene | Wounded vs. non-wounded control | Wounded & treated with HB2235 vs. wounded |
| Matrix proteins | | | |
| COL1A1 | Collagen I, alpha 1 | 1.3195 | 2.0279 |
| COL3A1 | Collagen III, alpha 1 | 1.0353 | 1.5369 |
| COL5A1 | Collagen V, alpha 1 | −1.1487 | 1.1647 |
| COL5A2 | Collagen V, alpha 2 | −1.1096 | 1.8921 |
| COL5A3 | Collagen V, alpha 3 | 1.8025 | 6.5887 |
| COL14A1 | Collagen XIV, alpha 1 | 1.0353 | 1.5369 |
| ITGB3 | Integrin beta 1 | 1.0353 | 1.5369 |
| Inflammatory pathway | | | |
| CXCL1 | Chemokine (C—X—C) ligand 1 | 1.3195 | −1.057 |
| CXCL2 | Chemokine (C—X—C) ligand 2 | 4.2871 | −1.7171 |
| CXCL5 | Chemokine (C—X—C) ligand 5 | 2.9282 | −3.9449 |
| CSF2 | Granulocyte-macrophage colony stimulating factor 2 | 1.8661 | −1.6021 |
| IL6ST | Interleukin 6 signal transducer | 1.9319 | 1.5369 |
| IL-1β | Interleukin 1, beta | 1.4641 | −1.3947 |
| MAPK3 | Mitogen-activated protein kinase 3 | 2.2974 | 1.8921 |
| Anti-inflammatory pathway | | | |
| IL-10 | Interleukin 10 | 1.0353 | 1.5369 |
| Growth factors | | | |
| EGF | Epidermal growth factor | 1.2746 | 1.434 |
| PDGFA | Platelet derived growth factor alpha polypeptide | −1.0353 | 1.434 |
| VTN | Vitronectin | 1.0000 | 5.7358 |
| VEGFA | Vascular endothelial growth factor A | −1.366 | 1.1647 |
| TGFB1 | Transforming growth factor-β1 | 1.2311 | 2.1735 |
| Proteases and inhibitors | | | |
| MMP1 | Matrix metallopeptidase 1 | 1.8025 | 1.1647 |
| CTSL2 | Cathepsin L2 | 1.1487 | −1.7171 |
| PLAT | Tissue plasminogen activator | 3.3636 | 1.2483 |
| PLAU | Urokinase plasminogen activator | 2.0000 | −1.1329 |
| PTGS2 | Prostaglandin G/H synthase and cyclooxygenase | 2.4623 | −1.7171 |
| SERPINE1 | Serpin peptidase inhibitor, clade E, member 1 | 2.1435 | −1.4948 |

All of the compositions or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention.

All patents and publications identified in this application are hereby incorporated by reference in their entirety.

REFERENCES

Bergers G, Coussens L M (2000). Extrinsic regulators of epithelial tumor progression: metalloproteinases. *Curr Opin Genet Dev.* 10:120-127

Easton D M, Nijnik A, Mayer M L, Hancock R E (2009). Review Potential of immunomodulatory host defense peptides as novel anti-infectives. *Trends Biotechnol.* 27(10):582-90.

Enoch S, Price P (2004). Cellular, molecular and biochemical differences in the pathophysiology of healing between acute wounds, chronic wounds and wounds in the aged. World Wide Wounds. (worldwidewounds.com/2004/august/Enoch/Pathophysiology-Of-Healing.html)

Gallo R L, Ono M. et al., (1994). Syndecans, cell surface heparin sulfate proteoglycans, are induced by a proline-rich antimicrobial peptide from wounds. *Proc Natl Acad Sci USA.* 91:11035-9

Heilborn J D, Nilsson M F. et al., (2003). The cathelicidin antimicrobial peptide LL-37 is involved in re-epithelialization of human skin wounds and is lacking in chronic ulcer epithelium. *J Invest Dermatol.* 120: 379-89

Lee P H, Rudisill B A et al., (2004). HB-107, a nonbacteriostatic fragment of the antimicrobial peptide cecropin B, accelerate murine wound repair. *Wound Rep Reg* 12: 351-8.

Leitch V D, Strudwick X L, Matthaei K I, Dent L A, Cowin A J. (2009). IL-5-overexpressing mice exhibit eosinophilia and altered wound healing through mechanisms involving prolonged inflammation. *Immunol Cell Biol.* 87(2): 131-40.

Mustoe T A, Cutler N R, Allman R M, Goode P S, et al., (1994) A phase II study to evaluate recombinant platelet-derived growth factor-BB in the treatment of stage 3 and 4 pressure ulcers. *Ach Surg* 129: 213-9.

Nijnik A, Madera L, Ma S, Waldbrook M, Elliott M R, Easton D M, Mayer M L, Mullaly S C, Kindrachuk J, Jenssen H, Hancock R E (2010). Synthetic cationic peptide IDR-1002 provides protection against bacterial infections through chemokine induction and enhanced leukocyte recruitment. *J Immunol.* 184(5):2539-50.

Oono T, Shirafuji Y. et al., (2002). Effects of human neutrophil peptide-1 on the expression of interstitial collagenase and type I collagen in human dermal fibroblasts. *Arch Dermatol Res* 294:185-9

Presland R B, Dale B A (2000). Epithelial structural proteins of the skin and oral cavity: function in health and disease. *Crit. Rev. Oral Bio. Med.* 11:383-408

Proksch E, Brandner J M, Jensen J M (2008). The skin: an indispensable barrier. *Exp Dermatol.* 17:1063-72.

Robert L, Labat-Robert J and Robert A M (2009) Physiology of skin aging. *Pathol Biol (Paris).* 57(4):336-41.

Rogalski C et al., 2002. Extensive striae distensae as a result of topical corticosteroid therapy. Acta Derm Venereol, 83:54-55

Samah A (2011). Topically applied KTTKS: a review. *Int J Cosmet Sci.* 33: 483-90. Shi J, Ross C R, Leto T L, and Blecha F (1996) PR-39, a proline-rich antibacterial peptide that inhibits phagocyte NADPH oxidase activity by binding to Src homology 3 domains of p47 phox. *Proc Natl Cad Sci USA.* 93:6014-8

Singer, A. J., Clark, R. A. (1999). Cutaneous wound healing. *N. Engl. J. Med.* 341, 738-746

Steed D L (1995). Clinical evaluation of recombinant human platelet-derived growth factor for the treatment of lower extremity diabetic ulcers. Diabetic ulcer study group. *J Vasc Surg* 21:71-8.

Steinstraesser L, Koehler T, Jacobsen F, Daigeler A, Goertz O, Langer S, Kesting M, Steinau H, Eriksson E, Hirsch T (2008). Host defense peptides in wound healing. *Mol Med.* 14(7-8):528-37.

Steinstraesser L, Kraneburg U M, Hirsch T, Kesting M, Steinau H U, Jacobsen F, Al-Benna S (2009). Host defense peptides as effector molecules of the innate immune response: a sledgehammer for drug resistance? *Int J Mol Sci.* 10(9):3951-70.

Upton Z, Cuttle L, Noble A, Kempf M, Topping G, Malda J, et al., (2008) Vitronectin: growth factor complexes hold potential as a wound therapy approach. *J Invest Dermatol.* 128:1538-1544.

Wang, X J, Han G, Owens P, Siddiqui Y and Li A G (2006). Role of TGF beta-mediated inflammation in cutaneous wound healing. *J Investig Dermatol Symp Proc.* 11 (1): 112-7.

Zhang L, Falla T J (2006). Antimicrobial peptides: therapeutic potential. *Expert Opin Pharmacother.* 7(6):653-63.

---

What is claimed is:

1. An isolated peptide, wherein the sequence of the peptide consists of SEQ ID NO: 5 (MGRN) or SEQ ID NO: 2 (KMGRN), wherein the peptide is in free acid form, amidated at the carboxy terminus or lipidated at the amine terminus.

2. The peptide of claim 1 which is SEQ ID NO:5 (MGRN) or SEQ ID NO 2 (KMGRN), wherein the peptide is amidated at the carboxy terminus or lipidated at the amine terminus.

3. The peptide of claim 1 which comprises either or both L- and D-amino acid enantiomers.

4. A composition comprising at least one peptide according to claim 1 and a pharmaceutically acceptable carrier.

5. The composition of claim 4, wherein the peptide is present in a concentration ranging from 0.1 μg/mL to 500 μg/mL, or 0.1 μg/mL to 20 mg/mL.

6. The composition of claim 4, wherein the pharmaceutically acceptable carrier is an aerosol, emulsion, liquid, lotion, solution, gel, micro-encapsulation, cream, paste, ointment, powder or foam.

7. The composition of claim 4 wherein the peptide is SEQ ID NO:5 (MGRN) or SEQ ID NO: 2 (KMGRN) and wherein the peptide is amidated at the carboxy terminus or lipidated at the amine terminus.

8. A method of treating a wound of the skin or mucosal tissue of a mammal comprising applying to the wound site a composition comprising a peptide having the sequence selected from the group consisting of SEQ ID NO:4 (EKMG), SEQ ID NO:5 (MGRN) or SEQ ID NO: 2 (KMGRN).

9. The method of claim 8 wherein the peptide is SEQ ID NO:4 (EKMG) or SEQ ID NO:5 (MGRN) or SEQ ID NO: 2 (KMGRN).

10. The method of claim 8 wherein the peptide comprises either or both L- and D-amino acid enantiomers or is conjugated to a carrier molecule, amidated or lipidated.

11. The method of claim 8 wherein the peptide is in free acid form.

12. The method of claim 8 wherein the wound is due to an abrasion, blister, burn, laceration, ulcer, bruise, rash, scar, stretch mark or the effects of aging or environmental exposure.

* * * * *